US012728213B2

(12) United States Patent
Xie

(10) Patent No.: US 12,728,213 B2
(45) Date of Patent: Sep. 8, 2026

(54) GEAR PUMP FOR MICROVAPORIZER CARTRIDGE

(71) Applicant: Central Victory Limited HK, Hong Kong (CN)

(72) Inventor: Haojun Xie, Guangxi (CN)

(73) Assignee: CENTAL VICTORY LIMITED HK, Hong Kong (CN)

(*) Notice: Subject to any disclaimer, the term of this patent is extended or adjusted under 35 U.S.C. 154(b) by 1224 days.

(21) Appl. No.: 17/640,485

(22) PCT Filed: Sep. 6, 2019

(86) PCT No.: PCT/CN2019/104651
§ 371 (c)(1),
(2) Date: Mar. 4, 2022

(87) PCT Pub. No.: WO2021/042357
PCT Pub. Date: Mar. 11, 2021

(65) Prior Publication Data
US 2022/0347401 A1 Nov. 3, 2022

(51) Int. Cl.
*A61M 11/04* (2006.01)
*A24F 40/48* (2020.01)
(Continued)

(52) U.S. Cl.
CPC ........... *A61M 11/042* (2014.02); *A24F 40/48* (2020.01); *F04C 2/321* (2013.01); *A24F 40/10* (2020.01);
(Continued)

(58) Field of Classification Search
CPC ......... A61M 11/042; A61M 2205/3653; A24F 40/58; A24F 40/10; F04C 2/321; F04C 2240/20
(Continued)

(56) References Cited

U.S. PATENT DOCUMENTS 2,203,974 A * 6/1940 Weinhardt ................ F04C 2/44 415/217.1
3,289,591 A 12/1966 Gustaf
(Continued)

FOREIGN PATENT DOCUMENTS

CN 1541577 11/2004
CN 206197013 5/2017
(Continued)

OTHER PUBLICATIONS

Machine Translation of JP61175290A (Year: 1986).*
(Continued)

*Primary Examiner* — Charles G Freay
(74) *Attorney, Agent, or Firm* — NIXON & VANDERHYE, PC

(57) ABSTRACT

A pump (34) is configured to pressurize fluid in a microvaporizer (10). The pump includes a chamber (42) bounded by a chamber wall (43) with an inlet opening (55) configured to receive fluid and an outlet opening (57) configured to discharge fluid. The chamber has a circular cross-section. The pump further includes a rotatable impeller (44) positioned within the chamber and a shaft (46) extending through a center of the impeller. The impeller is configured to rotate around the central longitudinal axis of the shaft. In addition, the shaft is offset from the center of the chamber toward the outlet opening and away from the inlet opening so that the axis of rotation of the impeller is offset from the center of the chamber. The pump has a compact design that is able to generate the pressure differential necessary to maintain the flow of fluid and is able to react quickly to meet the demand of the user.

33 Claims, 5 Drawing Sheets

(51) Int. Cl.
*F04C 2/32* (2006.01)
*A24F 40/10* (2020.01)

(52) U.S. Cl.
CPC .. *A61M 2205/3653* (2013.01); *F04C 2240/20* (2013.01)

(58) Field of Classification Search
USPC .......................................................... 418/259
See application file for complete search history.

(56) References Cited

U.S. PATENT DOCUMENTS

| | | | | |
|---|---|---|---|---|
| 4,392,779 | A * | 7/1983 | Bloemers | F04C 2/44 415/217.1 |
| 4,930,997 | A | 6/1990 | Bennett | |
| 6,292,970 | B1 * | 9/2001 | Rief | E04H 4/1654 15/387 |

FOREIGN PATENT DOCUMENTS

| | | | |
|---|---|---|---|
| CN | 107455800 | | 12/2017 |
| CN | 109077359 | | 12/2018 |
| CN | 208492886 | | 2/2019 |
| GB | 2542018 | | 3/2017 |
| JP | 61175290 | A * | 8/1986 |

OTHER PUBLICATIONS

International Search Report for PCT/CN2019/104651, mailed Jun. 15, 2020, 6 pages.
Written Opinion of the ISA for PCT/CN2019/104651, mailed Jun. 15, 2020, 4 pages.

* cited by examiner

GEAR PUMP FOR MICROVAPORIZER CARTRIDGE

This application is the U.S. national phase of International Application No. PCT/CN2019/104651 filed 6 Sep. 2019 which designated the U.S., the entire contents of each of which are hereby incorporated by reference.

TECHNICAL FIELD

The invention relates to a gear pump, and particularly to gear pump for a microvaporizer cartridge.

BACKGROUND

Microvaporizers (also referred to a vaping devices) are often used to dispense one or more active substances using the vaporized material. In atmospheric dispensers the substances may include materials such as deodorizing fragrance, medicine, nicotine, and insect repellent. In the case of personal vaporizers the active substances typically include a flavor and/or nicotine. The flavor and nicotine strength can be dialed up or down so as to mimic a traditional smoking experience. In general the vaporized material is the sole source of active substances in the micovaporizor.

Microvaporizers are compact, handheld devices that include reservoirs of fluid. In order for the fluid to be vaporized, the fluid must be delivered to a heater. Several methods may be used to generate the flow of the fluid to the heater. One such method utilizes a pump to generate the flow of fluid. However, this pump must be compact and capable of generating the pressure differential necessary to maintain the flow of fluid without overwhelming heater. In addition, the pump must be able to actuate and generate the pressure differential quickly in order to meet demand.

BRIEF SUMMARY

The pump described herein attempts to improve the deficiencies of conventional pumps. For example, the pump has a compact design that is able to generate the pressure differential necessary to maintain the flow of fluid and is able to react quickly to meet the demand of the user.

In a first aspect of the technology, a pump may be configured to pressurize fluid in a microvaporizer. The pump may include a chamber bounded by a chamber wall, a rotatable impeller positioned within the chamber, and a shaft extending through a center of the impeller.

The chamber wall may include an inlet configured to receive fluid and an outlet configured to discharge fluid. In addition, the chamber may have a circular cross-section. The impeller may be configured to rotate around the central longitudinal axis of the shaft, the shaft may be offset from the center of the chamber toward the outlet and away from the inlet so that the axis of rotation of the impeller is offset from the center of the chamber.

The impeller may be constructed from a flexible material and may be deformable.

The impeller may be positioned so that a wall of the chamber located proximate the outlet deforms the impeller.

The impeller may be compressed against a wall of the chamber located proximate the outlet.

It is contemplated that the pump may further include a casing and the chamber may be located within the casing. The casing may also include an intake conduit configured to deliver the fluid to the chamber and a discharge conduit configured to discharge fluid from the chamber.

The intake conduit may be configured to be fluidly connected to a reservoir of the microvaporizer.

The discharge conduit may be configured to be fluidly connected to a heater of the microvaporizer.

In another aspect of the technology, a cartridge for a microvaporizer may include a main body, a reservoir located within the main body, and a heater attached to the main body. The cartridge may also include the pump discussed above.

In yet another aspect of the technology, a microvaporizer may include a base and the cartridge discussed above. The cartridge may be configured to be secured to the base.

In yet another aspect of the technology, a pump may be configured to pressurize fluid in a microvaporizer and may include a chamber bounded by a chamber wall and a rotatable impeller positioned within the chamber.

The chamber wall may have an inlet configured to receive fluid and may have an outlet configured to discharge fluid. In addition, the chamber may have a circular cross-section.

The impeller may have a plurality of flexible arms radiating outwardly from a central core. Each pair of neighboring flexible arms may form a sub-chamber with the chamber wall. A center of rotation of the impeller may be offset from the center of the chamber toward the outlet and away from the inlet. In addition, the flexible arms may be configured so that each sub-chamber continuously changes in volume as the impeller rotates.

The flexible aims may be configured so that the shape of each sub-chamber continuously changes as the impeller rotates.

The flexible aims may be configured so that the volume of each sub-chamber is at a maximum when the sub-chamber is positioned at the inlet.

Each sub-chamber may be configured to receive fluid from the inlet when the sub-chamber is positioned adjacent the inlet.

The flexible aims May be configured so that the volume of each sub-chamber is at a minimum when the sub-chamber is positioned at the outlet.

Each sub-chamber may be configured to discharge fluid to the outlet when the sub-chamber is positioned adjacent the outlet.

The impeller may be compressed against a wall of the chamber located proximate the outlet.

It is contemplated that the pump may further include a casing and the chamber may be located within the casing. The casing may also include an intake conduit configured to deliver the fluid to the chamber and a discharge conduit configured to discharge fluid from the chamber.

The intake conduit may be configured to be fluidly connected to a reservoir of the microvaporizer.

The discharge conduit may be configured to be fluidly connected to a heater of the microvaporizer.

In yet another aspect of the technology, a cartridge for a microvaporizer may include a main body, a reservoir located within the main body, and a heater attached to the main body. The cartridge may also include the pump discussed above.

In yet another aspect of the technology, a microvaporizer may include a base and the cartridge discussed above. The cartridge may be configured to be secured to the base.

In yet another aspect of the technology, a pump may be configured to pressurize fluid in a microvaporizer and may include a chamber bounded by a chamber wall, a rotatable impeller positioned within the chamber, and a shaft extending through a center of the impeller.

The chamber wall may include an inlet configured to receive fluid and an outlet configured to discharge fluid. The chamber may have a circular cross-section.

The impeller may have a plurality of flexible arms radiating outwardly from a central core. The impeller may be configured to rotate around the central longitudinal axis of the shaft. In addition, the shaft may be offset from the center of the chamber toward the outlet and away from the inlet so that the axis of rotation of the impeller is offset from the center of the chamber. Also, each flexible aim may be configured to gradually bend as the flexible arm approaches the outlet.

Each flexible arm may be configured to gradually unbend as the flexible arm approaches the inlet.

The impeller may be constructed from a flexible material.

Each flexible arm may be hinged.

Each flexible arm may include a living hinge.

The impeller may be positioned within the chamber so that the chamber wall causes each flexible arm to gradually bend as the flexible arm approaches the outlet.

It is contemplated that the pump may further include a casing and the chamber may be located within the casing. The casing may also include an intake conduit configured to deliver the fluid to the chamber and a discharge conduit configured to discharge fluid from the chamber.

The intake conduit may be configured to be fluidly connected to a reservoir of the microvaporizer.

The discharge conduit may be configured to be fluidly connected to a heater of the microvaporizer.

In yet another aspect of the technology, a cartridge for a microvaporizer may include a main body, a reservoir located within the main body, and a heater attached to the main body. The cartridge may also include the pump discussed above.

In yet another aspect of the technology, a microvaporizer may include a base and the cartridge discussed above. The cartridge may be configured to be secured to the base.

DETAILED DESCRIPTION

Figure 1:
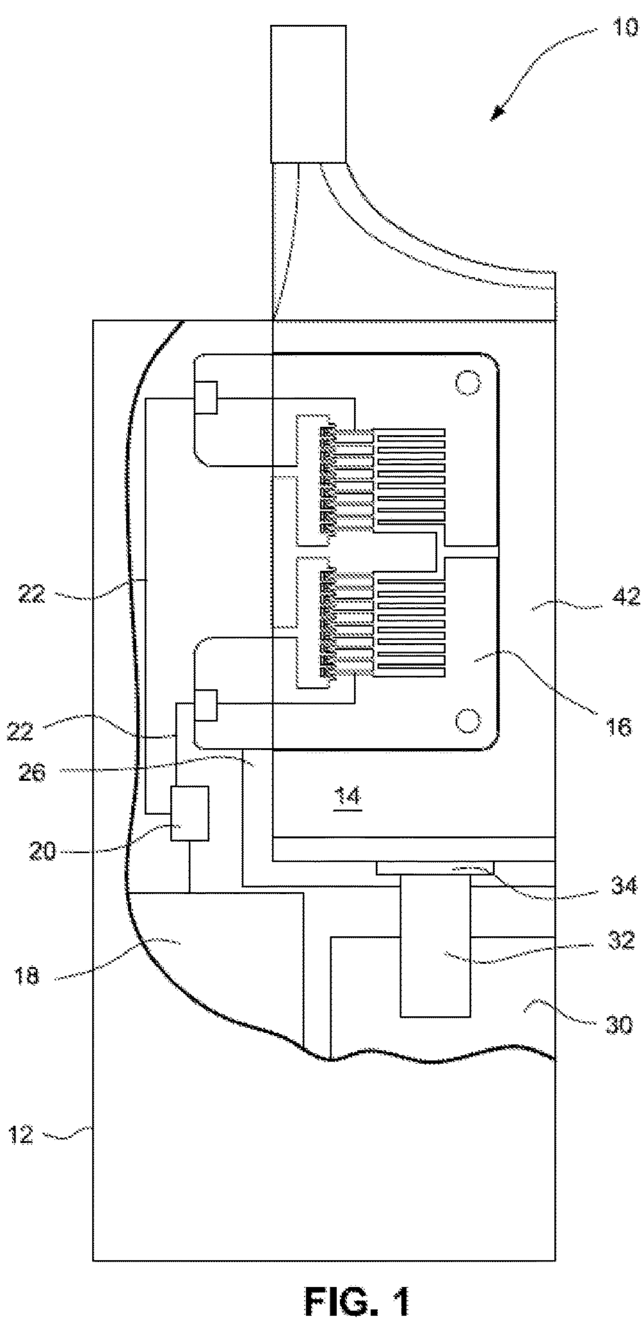
FIG. 1 shows an exemplary microvaporizer including a base, cartridge and heater, with a portion of a sidewall of the base removed to show the cartridge and heater.

FIG. 1 shows a microvaporizer 10 for generating an aerosol for inhalation by a user. The microvaporizer 10 may be configured as a vaping device for delivery of a nicotine vapor to the mouth of a user. The microvaporizer 10 may also be configured to deliver a medicinal vapor, such as an aerosol infused with asthma drugs, to the mouth of a user. Moreover, the microvaporizer 10 may be configured for use to deliver other types of vapor (aerosols) to a user.

The microvaporizer 10 may include a base 12, a cartridge 14 and a heater 16. The base 12 may be a hollow handheld device. The outer surfaces of the base 12 may be shaped to be easily held in one hand and carried in a user's pocket or purse.

The base 12 may house a battery 18, electronic circuits 20 and electrical conductors 22 that connect the battery 18 to the electronic circuits 20 and the heater 16. The electronic circuits 20 may control delivery of electrical power from the battery 18 to resistive heating elements 24 in the heater 16.

Figure 2:
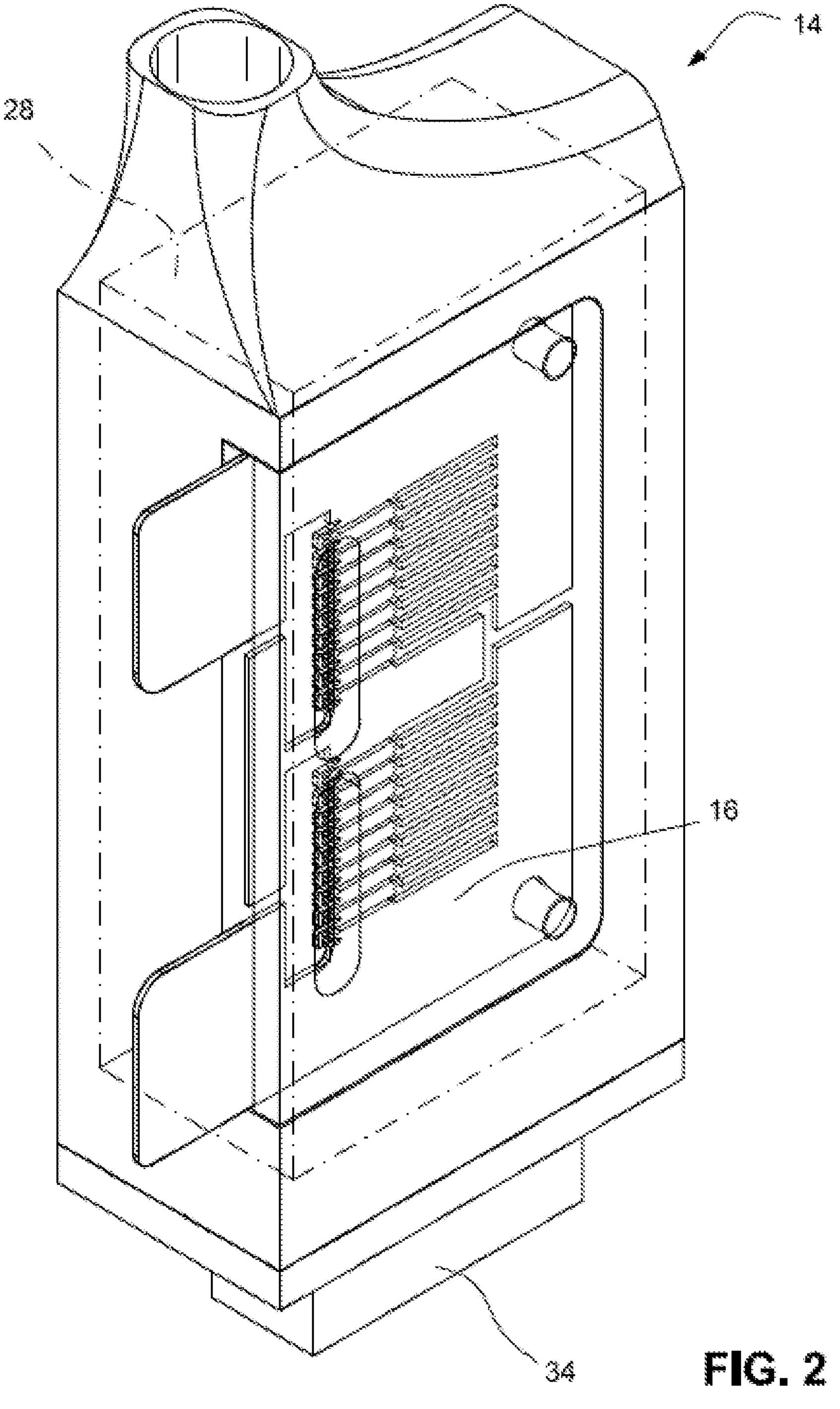
FIG. 2 is a perspective view of the cartridge and heater shown in FIG. 1.

The base 12 may also house a secondary reservoir 26 which may provide fluid to the cartridge 14. The secondary reservoir 26 may be internal to the base 12 and may be behind a mount (not shown) for the cartridge 14. The secondary reservoir 26 may be optional. It is contemplated that the secondary reservoir 26 may be in addition to a primary reservoir 28 (see FIGS. 2 and 3) in the cartridge 14 if the primary reservoir 28 is too small to store enough fluid to generate vapor for an extended period, such as several days. It is further contemplated that the primary reservoir 28 may be omitted and the secondary reservoir 26 in the base 12 may be the only reservoir in the microvaporizer 10.

The base 12 may also include a motor 30 to drive a drive shaft 32 of a pump 34 in the cartridge 14. The pump 34 may pump fluid from the cartridge 14 into and through the heater 16 and/or pump fluid from the secondary reservoir 26 into the primary reservoir 28. It is contemplated that the pump 34 may be actuated by a user input device such as a button, switch or pressure sensor (not shown) on the cartridge 14 or on the base 12. Alternatively, the pump 34 may be actuated by the user's inhalation (e.g., by way of a pressure or flow sensor (not shown) in the cartridge. It is further contemplated that the pump 34 may pump fluid from the secondary reservoir 26 into the primary reservoir 28 once a certain period of time, e.g., 20 to 120 seconds, has elapsed since the last inhaling action by the user. It is further contemplated that the pump 34 may pump unused fluid from the heater 16 into the primary reservoir 28 and/or the secondary reservoir 26.

Figure 3:
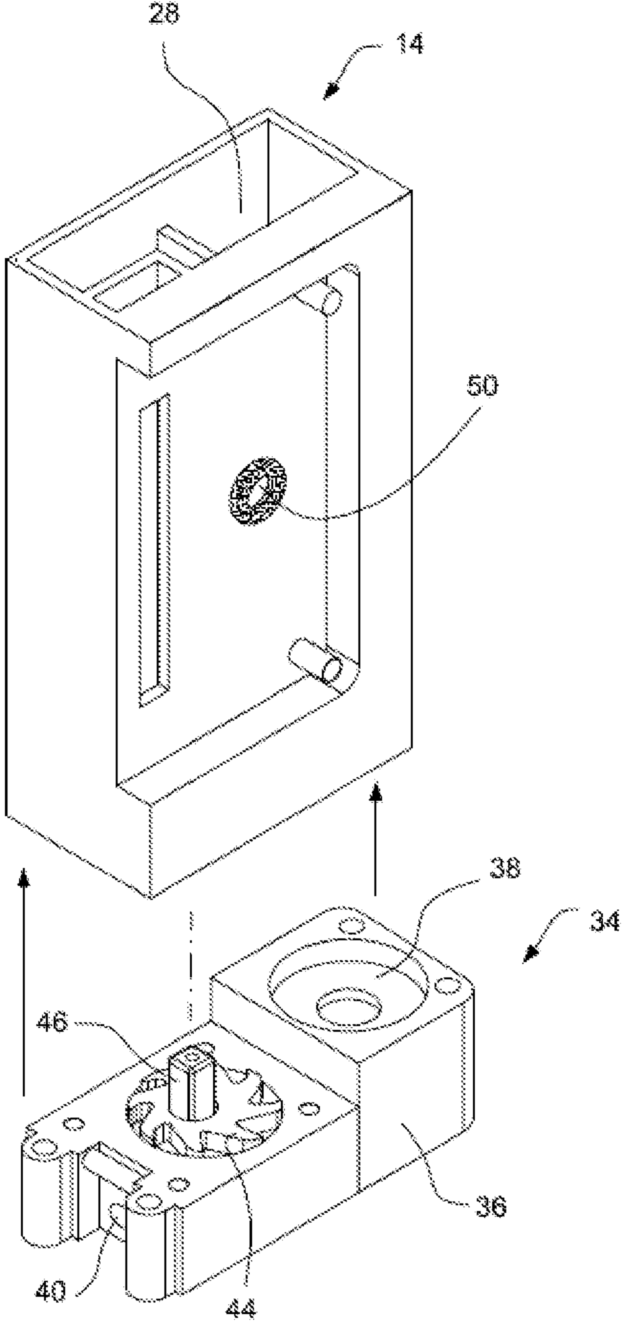
FIG. 3 is an exploded view of the cartridge with an exemplary pump.
Figure 4:
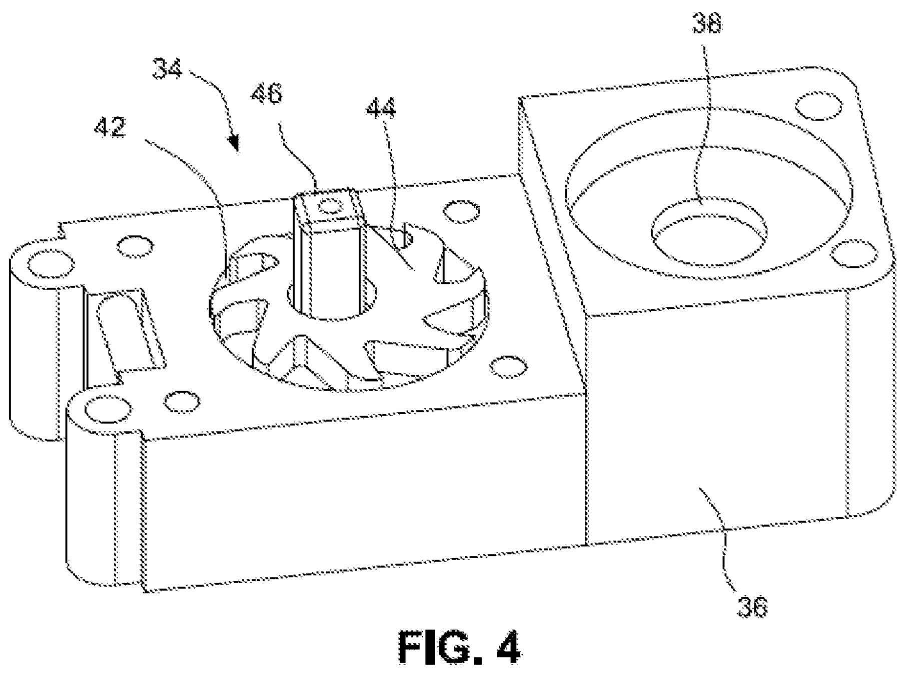
FIG. 4 is a perspective view of the pump of FIG. 3.
Figure 5:
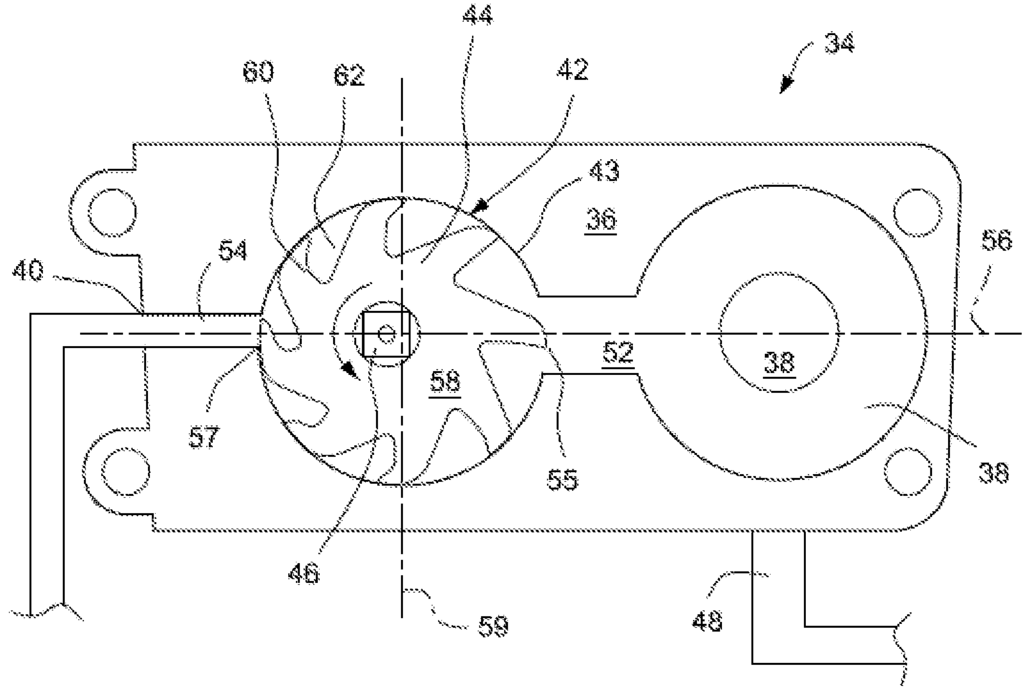
FIG. 5 is a schematic view of the pump of FIG. 3

As shown in FIGS. 3-5, the pump 34 may have a housing (or casing) 36 that may be attached to the cartridge 14. It is contemplated that the housing 36 may be unitarily foamed with the cartridge 14 and/or may be housed within the cartridge 14. Alternatively, the pump may be formed separately from the cartridge 14 and may be attached (either permanently or removably) to a side or bottom of the cartridge 14. The pump 34 may further include an inlet 38, an outlet 40, an impeller chamber 42, an impeller (or gear) 44, and a shaft 46.

The inlet 38 may be an opening in the housing (or casing) 36 that is positioned to receive fluid from the primary reservoir 28 and/or the secondary reservoir 26. It is contemplated that if the inlet 38 is configured to receive fluid from the secondary reservoir, the inlet 38 may receive the fluid by way of a supply conduit 48. The outlet 40 may be an opening in the housing (or casing) 36 that is positioned to deliver pressurized fluid to an opening 50 in the cartridge 14. The opening 50 may be connected to an inlet (not shown) of the heater 16.

The impeller chamber 42 may be bound by a chamber wall 43 and may contain the impeller 44 and the shaft 46. The impeller chamber 42 may be substantially cylindrical in shape or at least have a circular cross-section. The impeller chamber 42 may receive fluid from the inlet 38 by way of an intake conduit (or flow path) 52 and may discharge pressurized fluid to the outlet 40 by way of a discharge conduit (or flow path) 54. The intake conduit 52 may teammate at an inlet opening 55 in the chamber wall 43. In addition, the discharge conduit 54 may begin at an outlet opening 57 in the chamber wall 43. It is contemplated that the intake and discharge conduits 52, 54 as well as the inlet and outlet openings 55, 57 may be centered along a line 56 that extends through the center of the circular cross-section of the impeller chamber 42. It is further contemplated that the inlet and outlet openings 55, 57 may oppose each other.

The shaft 46 may be an extension of the drive shaft 32 and may be centered on the line 56. The shaft 46 may also be offset from a line 59 that is perpendicular to the line 56 and extends through the center of the circular cross-section of the impeller chamber 42. The offset of the shaft 46 may be toward the outlet opening 57 and away from the inlet opening 55 so that the distance between the shaft 46 and the outlet opening 57 is less than the distance between the shaft 46 and the inlet opening 55. Due to the location of the shaft 46, the axis of rotation of the impeller 44 may be offset from the center of the circular cross-section of the impeller chamber 42.

The impeller 44 may be unitarily formed from a flexible material. For example, the impeller 44 may be formed of silicone, rubber, or any other flexible material. The impeller 44 may have a core portion 58 and a plurality of flexible (or deformable) arms (teeth) 60 extending from the core portion 58. Each flexible arm 60 may extend to the chamber wall 43 so that each pair of neighboring arms 60 may form a sub-chamber (or void) 62 with the chamber wall 43. Each sub-chamber 62 may receive fluid from the intake conduit 54 by way of the inlet opening 55 and may dispense the fluid into the discharge conduit 54 by way of the outlet opening 57.

The impeller 44 may be sized so that the diameter of the impeller 44 prior to being installed in the impeller chamber 42 is larger than the diameter of the impeller chamber 42. In order to install the impeller 44 into the impeller chamber 42, the impeller 44 may be squeezed to reduce the diameter of the impeller 44. Due to the offset position of the shaft 46 (which may support the impeller 44 at the center of the impeller 44) and the smaller diameter of the impeller chamber 42, the portion of the chamber wall 43 proximate to the outlet opening 57 may compress or deform the flexible arms 60 of the impeller 44.

Figure 6:
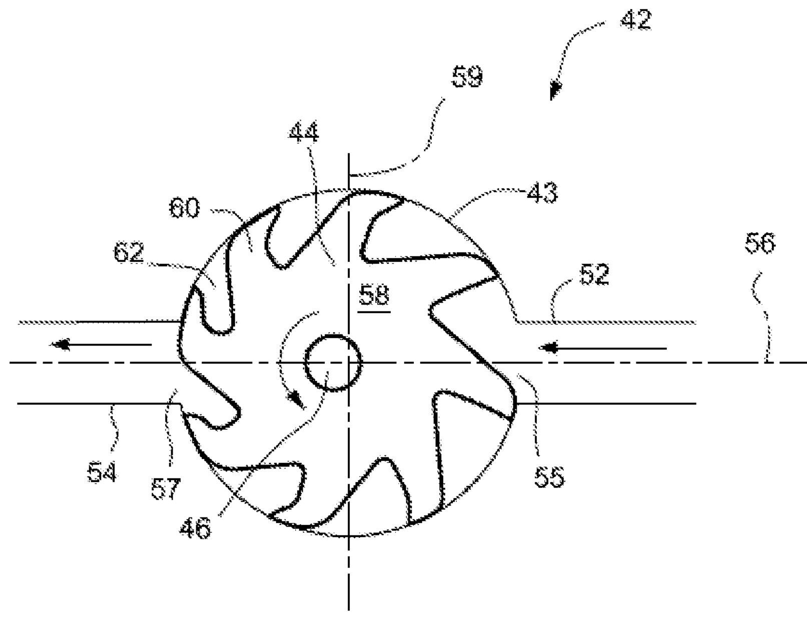
FIG. 6 is a schematic view of an impeller for the pump of FIG. 3

As can be seen in FIGS. 5 and 6, the maximum distance between the shaft 46 and the chamber wall 43 may be at the inlet opening 55. At the same time, the minimum distance between the shaft 46 and the chamber wall 43 may be at the outlet opening 57. Thus, as the impeller rotates, the amount of space available in the impeller chamber 42 for each flexible arm 60 may gradually increase or decrease depending on the location of the flexible arm 60. In particular, as the flexible aims 60 rotate from the inlet opening 55 toward the outlet opening 57, the amount of space available in the impeller chamber 42 for the flexible arms 60 may decrease. Conversely, as the flexible arms 60 rotate from the outlet opening 57 toward the inlet opening 55, the amount of space available in the impeller chamber 42 for the flexible aims 60 may increase. As such, as the flexible aims 60 rotate toward the outlet opening 57 (away from the inlet opening 55), the amount by which the flexible arms 60 are bent may gradually increase until the flexible arm 60 reaches the outlet opening 57 when the flexible arm 60 may be bent to its furthest extent. As the flexible arms 60 rotate toward the inlet opening 55 (away from the outlet opening 57), the amount by which the flexible arms 60 are bent may gradually decrease until the flexible arm 60 reaches the inlet opening 55 when the flexible aim 60 may be bent to its least extent (if at all).

As can be seen in FIG. 5, it is contemplated that the flexible arms 60 may be bent toward a direction that is opposite to the direction of the rotation of the impeller 44. In addition, the flexible aims 60 may always be bent even at the location adjacent to the inlet opening 55 in order to minimize or avoid the possibility of a flexible arm 60 fully extending and getting stuck against the chamber wall 43. Although the figures show the flexible arms 60 being flexed, the flexible arms 60 may be hinged or may have living hinges. Also, although the figures show the flexible arms 60 being may of a single unitary piece, the flexible arms 60 may be made of multiple sub-components, and the flexible arms 60 may be bent at an interface between the sub-components of the flexible aims 60.

As the extent to which the flexible arms 60 are bent changes, the volume and the shape of the sub-chambers 62 may also change. In particular, as the sub-chambers 62 rotate toward the outlet opening 57 (away from the inlet opening 55), the volume of each sub-chamber 62 may gradually decrease until the sub-chamber 62 reaches the outlet opening 57 when the volume of the sub-chamber 62 may be smallest. As sub-chambers 62 rotate toward the inlet opening 55 (away from the outlet opening 57), the volume of each sub-chamber 62 may gradually increase until the sub-chamber 62 reaches the inlet opening 55 when the volume of the sub-chamber 62 may be largest.

The reduction in the volume of each sub-chamber 62 as each sub-chamber 62 rotates toward the outlet opening 57 may gradually increase the pressure on the fluid until the fluid is released in to the discharge conduit 54 by way of the outlet opening 57. Such a change in pressure may allow the pump 34 to pressurize the fluid without substantially increasing the flow of the fluid through the pump 34 as well as the microvaporizer 10.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A pump configured to pressurize fluid in a microvaporizer, the pump comprising:

a chamber bounded by a chamber wall with an inlet opening configured to receive fluid and an outlet opening configured to discharge fluid, the chamber having a circular cross-section;

a rotatable impeller positioned within the chamber; and a shaft extending through a center of the impeller, the impeller being configured to rotate around the central longitudinal axis of the shaft, the inlet opening, the outlet opening and the shaft being centered on a line extending through the chamber, wherein the shaft is offset from the center of the chamber toward the outlet opening and away from the inlet opening so that the axis of rotation of the impeller is offset from the center of the chamber so that the shaft is closer to the center of the outlet opening than to the center of the inlet opening.

2. The pump of claim 1, wherein the impeller is constructed from a flexible material.

3. The pump of claim 1, wherein the impeller is deformable.

4. The pump of claim 1, wherein the impeller is positioned so that a wall of the chamber located proximate the outlet opening deforms the impeller.

5. The pump of claim 1, wherein the impeller is compressed against a wall of the chamber located proximate the outlet opening.

6. The pump of claim 1, further comprising a casing that comprises the chamber, wherein the casing further comprises:

an intake conduit configured to deliver the fluid to the chamber; and a discharge conduit configured to discharge fluid from the chamber.

7. The pump of claim 6, wherein the intake conduit is configured to be fluidly connected to a reservoir of the microvaporizer.

8. The pump of claim 6, wherein the discharge conduit is configured to be fluidly connected to a heater of the microvaporizer.

9. A cartridge for a microvaporizer, the cartridge comprising:

a main body;

a reservoir located within the main body;

a heater attached to the main body; and the pump of claim 1.

10. A microvaporizer comprising:

a base; and the cartridge of claim 9, the cartridge being configured to be secured to the base.

11. A pump configured to pressurize fluid in a microvaporizer, the pump comprising:

a chamber bounded by a chamber wall with an inlet opening configured to receive fluid and an outlet opening configured to discharge fluid, the chamber having a circular cross-section; and a rotatable impeller positioned within the chamber, the impeller having a plurality of flexible arms radiating outwardly from a central core, each pair of neighboring flexible arms forming a sub-chamber with the chamber wall, the inlet opening, the outlet opening, and a center of rotation of the impeller being centered on a line extending through the chamber;

wherein the center of rotation of the impeller is offset from the center of the chamber toward the outlet opening and away from the inlet opening so that the center of rotation of the impeller is closer to the center of the outlet opening than to the center of the inlet opening, and wherein the flexible arms are configured so that each sub-chamber continuously changes in volume as the impeller rotates.

12. The pump of claim 11, wherein the flexible arms are configured so that the shape of each sub-chamber continuously changes as the impeller rotates.

13. The pump of claim 11, wherein the flexible arms are configured so that the volume of each sub-chamber is at a maximum when the sub-chamber is positioned at the inlet opening.

14. The pump of claim 13, wherein each sub-chamber is configured to receive fluid from the inlet opening when the sub-chamber is positioned adjacent the inlet opening.

15. The pump of claim 11, wherein the flexible arms are configured so that the volume of each sub-chamber is at a minimum when the sub-chamber is positioned at the outlet opening.

16. The pump of claim 15, wherein each sub-chamber is configured to discharge fluid to the outlet opening when the sub-chamber is positioned adjacent the outlet opening.

17. The pump of claim 11, wherein the impeller is compressed against a wall of the chamber located proximate the outlet opening.

18. The pump of claim 11, further comprising a casing that comprises the chamber, wherein the casing further comprises:

an intake conduit configured to deliver the fluid to the chamber; and a discharge conduit configured to discharge fluid from the chamber.

19. The pump of claim 18, wherein the intake conduit is configured to be fluidly connected to a reservoir of the microvaporizer.

20. The pump of claim 18, wherein the discharge conduit is configured to be fluidly connected to a heater of the microvaporizer.

21. A cartridge for a microvaporizer, the cartridge comprising:

a main body;

a reservoir located within the main body;

a heater attached to the main body; and the pump of claim 11.

22. A microvaporizer comprising:

a base; and the cartridge of claim 21, the cartridge being configured to be secured to the base.

23. A pump configured to pressurize fluid in a microvaporizer, the pump comprising:

a chamber bounded by a chamber wall with an inlet opening configured to receive fluid and an outlet opening configured to discharge fluid, the chamber having a circular cross-section;

a rotatable impeller positioned within the chamber, the impeller having a plurality of flexible arms radiating outwardly from a central core; and a shaft extending through a center of the impeller, the impeller being configured to rotate around the central longitudinal axis of the shaft, the inlet opening, the outlet opening and the shaft being centered on a line extending through the chamber, wherein the shaft is offset from the center of the chamber toward the outlet opening and away from the inlet opening so that the axis of rotation of the impeller is offset from the center of the chamber and is closer to the center of the outlet opening than to the center of the inlet opening, and wherein each flexible arm is configured so that an extent to which each flexible arm is bent gradually increases as the flexible arm approaches the outlet opening.

24. The pump of claim 23, wherein each flexible arm is configured so that the extent to which each flexible arm is bent gradually decreases as the flexible arm approaches the inlet opening.

25. The pump of claim 23, wherein the impeller is constructed from a flexible material.

26. The pump of claim 23, wherein each flexible arm is hinged.

27. The pump of claim 26, wherein each flexible arm comprises a living hinge.

28. The pump of claim 23, wherein the impeller is positioned within the chamber so that the chamber wall causes the extent to which each flexible arm is bent to gradually increase as the flexible arm approaches the outlet opening.

29. The pump of claim 23, further comprising a casing that comprises the chamber, wherein the casing further comprises:

an intake conduit configured to deliver the fluid to the chamber; and a discharge conduit configured to discharge fluid from the chamber.

30. The pump of claim 29, wherein the intake conduit is configured to be fluidly connected to a reservoir of the microvaporizer.

31. The pump of claim 29, wherein the discharge conduit is configured to be fluidly connected to a heater of the microvaporizer.

32. A cartridge for a microvaporizer, the cartridge comprising:

a main body;

a reservoir located within the main body;

a heater attached to the main body; and the pump of claim 23.

33. A microvaporizer comprising:

a base; and the cartridge of claim 32, the cartridge being configured to be secured to the base.

* * * * *